(12) United States Patent
Jesper et al.

(10) Patent No.: US 10,879,477 B2
(45) Date of Patent: Dec. 29, 2020

(54) CYCLIC AMINE SURFACE MODIFIER AND ORGANIC ELECTRONIC DEVICES COMPRISING SUCH CYCLIC AMINE SURFACE MODIFIER

(71) Applicants: MERCK PATENT GMBH, Darmstadt (DE); INNOVATIONLAB GMBH, Heidelberg (DE); TECHNISCHE UNIVERSITAET BRAUNSCHWEIG, Braunschweig (DE); MAX-PLANCK-GESELLSCHAFT ZUR FOERDERUNG DER WISSENSCHAFTEN E.V., Munich (DE)

(72) Inventors: Malte Jesper, Heidelberg (DE); Manuel Hamburger, Mannheim (DE); Janusz Schinke, Braunschweig (DE); Milan Alt, Heidelberg (DE); Klaus Muellen, Cologne (DE)

(73) Assignees: MERCK PATENT GMBH, Darmstadt (DE); INNOVATIONLAB GMBH, Heidelberg (DE); TECHNISCHE UNIVERSITAET BRAUNSCHWEIG, Braunschweig (DE); MAX-PLANCK-GESELLSCHAFT ZUR FOERDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 15/119,959

(22) PCT Filed: Feb. 16, 2015

(86) PCT No.: PCT/EP2015/000338
§ 371 (c)(1),
(2) Date: Aug. 18, 2016

(87) PCT Pub. No.: WO2015/124284
PCT Pub. Date: Aug. 27, 2015

(65) Prior Publication Data
US 2017/0062744 A1    Mar. 2, 2017

(30) Foreign Application Priority Data

Feb. 19, 2014 (EP) .................................... 14000575
Aug. 6, 2014 (EP) .................................... 14002743

(51) Int. Cl.
| | | |
|---|---|---|
| H01L 51/50 | (2006.01) |
| H01L 51/10 | (2006.01) |
| C07D 455/04 | (2006.01) |
| C07D 221/14 | (2006.01) |
| C07D 471/06 | (2006.01) |
| H01L 51/00 | (2006.01) |
| H01L 51/44 | (2006.01) |
| H01L 51/05 | (2006.01) |
| H01L 51/52 | (2006.01) |

(52) U.S. Cl.
CPC .......... H01L 51/105 (2013.01); C07D 221/14 (2013.01); C07D 455/04 (2013.01); C07D 471/06 (2013.01); H01L 51/0053 (2013.01); H01L 51/0072 (2013.01); H01L 51/0036 (2013.01); H01L 51/0541 (2013.01); H01L 51/0545 (2013.01); H01L 51/0558 (2013.01); H01L 51/441 (2013.01); H01L 51/5203 (2013.01)

(58) Field of Classification Search
CPC ............................. C07D 471/04; H01L 51/00
USPC ............................. 546/94, 95; 313/503, 504
See application file for complete search history.

(56) References Cited

U.S. PATENT DOCUMENTS

| | | | |
|---|---|---|---|
| 3,330,834 A | | 7/1967 | Senshu et al. |
| 5,514,505 A | * | 5/1996 | Limburg ................. G03G 17/04 430/41 |
| 7,485,733 B2 | * | 2/2009 | Kim ..................... C07D 333/08 252/301.16 |
| 7,670,870 B2 | | 3/2010 | Izumi et al. |
| 8,895,960 B2 | | 11/2014 | Murata et al. |
| 2012/0018706 A1 | | 1/2012 | Kagan et al. |

FOREIGN PATENT DOCUMENTS

| | | |
|---|---|---|
| JP | 2007311677 A | 11/2007 |
| JP | 2013055339 A | 3/2013 |
| WO | 03055853 A1 | 7/2003 |

OTHER PUBLICATIONS

Ishizaka, S.: Lasr emission from the organic free radical 9-jololidylthiyl in solution. Appl. Phys. B, vol. 48, pp. 111-113, 1989.*
International Search Report for PCT/EP2015/000338 dated Apr. 24, 2015.
Boudinet, D. et al., "Modification of gold source and drain electrodes by self-assembled monolayer in staggered n- and p-channel organic thin film transistors," Organic Electronics, Feb. 1, 2010, vol. 11, No. 2, pp. 227-237.
Masillamani, A. M. et al., "Multiscale Charge Injection and Transport Properties in Self-Assembled Monolayers of Biphenyl Thiols with Varying Torsion Angles," Chemistry—A European Journal, Jul. 24, 2012, vol. 18, No. 33, pp. 10335-10347.
Notification of reasons for refusal in corresponding JP 2016-553550 dispatched dispatched Feb. 15, 2019.

* cited by examiner

*Primary Examiner* — Charanjit Aulakh
(74) *Attorney, Agent, or Firm* — Millen White Zelano & Branigan (57) ABSTRACT

The present invention relates to a cyclic amine surface modifier. In addition the present invention also relates to organic electronic devices comprising such cyclic amine surface modifier.

12 Claims, 3 Drawing Sheets

CYCLIC AMINE SURFACE MODIFIER AND ORGANIC ELECTRONIC DEVICES COMPRISING SUCH CYCLIC AMINE SURFACE MODIFIER

TECHNICAL FIELD

The present invention relates to a cyclic amine surface modifier. In addition the present invention also relates to organic electronic devices comprising such cyclic amine surface modifier.

BACKGROUND

Organic electronic devices, such as for example organic thin film transistors, organic photovoltaic cells or organic light emitting devices, are substantially based on organic electronic materials, i.e. on materials being essentially carbon based. After intensive research efforts, both in academia and industry, a significant number of organic materials with desirable properties have been identified, ranging from small molecules to polymers.

However, for various reasons organic electronic devices are still mostly made with metal (or metal oxide) electrodes. One of the challenges in designing highly efficient organic electronic devices lies in matching the relative work functions of adjacent layers. While the properties of organic electronic materials can be adapted by changing their composition, for example by introducing substituents or by polymers comprising more than one monomer, such an adaptation is more difficult for metal (or metal oxide) electrodes. Additionally, other factors such as for example the adhesion between adjacent layers of an organic electronic device may also have an effect on the overall performance of such an organic electronic device.

In order to change the work function of metal (or metal oxide) electrodes, particularly of gold electrodes, and thus render them more easily compatible with organic electronic materials the metal (or metal oxide) electrodes may be covered with a self-assembled monolayer (SAM) of suitable molecules. For example, Boudinet et al. disclose in Organic Electronics 11 (2010) 227-237 the modification of gold source and drain electrodes with the following thiol compounds.

Self-assembled monolayers with stilbene-derivatives on gold have for example been disclosed by M. Malicki et al. in Langmuir 2009, 25(14), 7967-7975.

There is, however, still a need for further compounds that are suitable for such self-assembled monolayers.

It is therefore an object of the present invention to provide compounds that are suitable for such self-assembled monolayers. Preferably such compounds would also allow modifying the work function of metal or metal oxide electrodes of organic electronic devices. Other objects of the present invention will become evident from the following description and examples.

SUMMARY

The present inventors have now surprisingly found that the above objects may be attained either individually or in any combination by the self-assembled monolayer of the present application.

The present application therefore provides for a self-assembled monolayer comprising a moiety of general formula (I)

(I)

wherein
$X^1$ is selected from the group consisting of —$CH_2$—, —$CF_2$— and aromatic C—$R^5$;
$X^2$ is selected from the group consisting of —$CH_2$—, —$CF_2$— and —C(=O)—;
$X^3$ is selected from the group consisting of —$CH_2$—, —$CF_2$—, —C(=O)— and N—$R^6$;
$X^4$ is selected from the group consisting of —$CH_2$—, —$CF_2$—, —C(=O)— and N—$R^7$;
$R^1$ and—if present—$R^6$ are independently of each other selected from the group consisting of H, F, methyl, ethyl, methyl wherein one or more hydrogen is replaced by fluorine, ethyl wherein one or more hydrogen is replaced by fluorine, and —(C≡C)$_a$—(Ar$^1$)$_b$—(C≡C)$_c$—(R$^8$)$_d$—$X^5$—* with
$Ar^1$ being para-phenylene or a para-phenylene wherein one or more carbon ring atom is substituted by N;
$R^8$ being —$CH_2$— or —$CF_2$—;
$X^5$ being selected from the group consisting of —$X^a$—, —$X^a$—$X^b$—, —C(=$X^a$)—$X^b$—, —$X^a$O$_3$—, —$X^a$—$X^b$O$_3$—, —PO$_2$H— and —PO$_3$H—, with $X^a$ and $X^b$ being independently of each S or Se;
a being 0, 1 or 2;
b being 0, 1 or 2;
c being 0, 1 or 2; and
d being 0, 1 or 2,
provided that if $X^3$ is NR$^6$ $R^1$ and $R^6$ are not both —(C≡C)$_a$—(Ar$^1$)$_b$—(C≡C)$_c$—(R$^8$)$_d$—$X^5$—*; and
$R^2$, $R^3$, $R^4$, $R^5$ and $R^7$ are independently of each other selected from the group consisting of H, F, methyl, ethyl, methyl wherein one or more hydrogen is replaced by fluorine, ethyl wherein one or more hydrogen is replaced by fluorine, and two or three neighboring groups of $R^2$, $R^3$, $R^4$, $R^5$ and $R^7$ may together form an aliphatic or aromatic ring system having a total of from 6 to 24 aromatic ring atoms.

The present application also provides for a metal or metal oxide surface modified by means of said self-assembled monolayer. Preferably said metal or metal oxide surface is an electrode.

Further, the present application provides for an organic electronic device comprising said self-assembled monolayer.

Furthermore, the present application also provides for a process for producing such self-assembled monolayer and also such organic electronic device.

DETAILED DESCRIPTION

For the purposes of the present application the term "self-assembled monolayer" is used in a non-limiting way to denote a layer as defined herein. The term "self-assembled monolayer" is used to help distinguish this layer from any other layer that might be mentioned in the present application.

In general terms the present application provides for a self-assembled monolayer comprising a moiety of general formula (I)

(I)

wherein $X^1$, $X^2$, $X^3$, $X^4$, $R^1$, $R^2$, $R^3$ and $R^4$ are as defined below.

$X^1$ is selected from the group consisting of —$CH_2$—, —$CF_2$— and aromatic C—$R^5$, with $R^5$ as defined below.

$X^2$ is selected from the group consisting of —$CH_2$—, —$CF_2$— and —C(=O)—.

$X^3$ is selected from the group consisting of —$CH_2$—, —$CF_2$— and N—$R^6$, with $R^6$ as defined below.

$X^4$ is selected from the group consisting of —$CH_2$—, —$CF_2$—, —C(=O)— and N—$R^7$, with $R^7$ as defined below.

$X^1$, $X^2$, $X^3$ and $X^4$ may be selected independently of each other, provided that either $X^3$ is N—$R^6$ or $X^4$ is N—$R^7$.

It is preferred that $X^1$ is C—$R^5$, $X^2$ is —C(=O)—, $X^3$ is N—$R^6$ and $X^4$ is —C(=O)— or that $X^1$ is —$CH_2$—, $X^2$ is —$CH_2$—, $X^3$ is —$CH_2$— and $X^4$ is $NR^7$, with $R^5$, $R^6$ and $R^7$ as defined below.

$R^1$ and—if present—$R^6$ are independently of each other selected from the group consisting of H, F, methyl, ethyl, methyl wherein one or more hydrogen is replaced by fluorine, ethyl wherein one or more hydrogen is replaced by fluorine, and —(C≡C)$_a$—(Ar$^1$)$_b$—(C≡C)$_c$—(R$^8$)$_d$—X$^5$—* with Ar$^1$, R$^8$, X$^5$, a, b, c and d as defined below, provided that if $X^3$ is N—$R^6$ $R^1$ and $R^6$ are not both —(C≡C)$_a$—(Ar$^1$)$_b$—(C≡C)$_c$—(R$^8$)$_d$—X$^5$—*.

Ar$^1$ is para-phenylene or para-phenylene wherein one or more carbon ring atoms are substituted by N. Examples of suitable Ar$^1$ may be selected from the group consisting of the following (II-1)

(II-2)

(II-3)

(II-4)

(II-5)

(II-6)

(II-7)

which may be used in either direction, i.e. with either * in the direction of the functional group $X^5$ of the moiety of formula (I). Of these para-phenylene (II-1) is preferred. Optionally, one or more of the hydrogen present on Ar$^1$ may be replaced by fluorine.

$R^5$ is —$CH_2$— or —$CF_2$—. Preferably $R^5$ is —$CH_2$—.

Functional group $X^5$ is selected from the group consisting of —$X^a$—, —$X^a$—$X^b$—, —C(=$X^a$)—$X^b$—, —$X^a$O$_3$—, —$X^a$—$X^b$O$_3$—, —PO$_2$H— and —PO$_3$H—, with $X^a$ and $X^b$ being independently of each S or Se. Preferably $X^5$ is selected from the group consisting of —S—, —S—S—, —C(=S)—S—, —SO$_3$—, —S—SO$^3$—, —PO$_2$H— and —PO$_3$H—. Most preferably $X^5$ is —S—.

It is noted that with regards to functional group $X^1$ selected from the group consisting of —$X^a$O$_3$—, —$X^a$—$X^b$O$_3$—, —PO$_2$H— and —PO$_3$H— a number of possible binding modes between $X^1$ and the metal or metal oxide surface may be envisaged. Without wishing to be bound by theory it is believed that generally the bonding between these functional groups $X^1$ and the metal or metal oxide surface is done by means of —O—. An example of such bonding is Metal-O—P—. These functional groups $X^1$ may for example be bound to the metal or metal oxide surface by means of one or more groups —O—. It is also possible that more than one such binding modes exist simultaneously.

Parameter a is 0, 1 or 2. Preferably a is 0 or 1.
Parameter b is 0, 1, or 2. Preferably b is 0 or 1.
Parameter c is 0, 1, or 2. Preferably c is 0 or 1.
Parameter d is 0, 1, or 2. Preferably d is 0 or 1.
Preferably at least one of parameters a, b, c and d is 1, i.e. a+b+c+d≥1.

Preferred combinations of a, b, c and d may be selected from the following:
(i) a+c is 1; preferably a is 1 and c is 0.
(ii) a, b and d are all 1; and c is 0.
(iii) d is 1; and a, b and c are all 0.
(iv) a, b, c and d are all 1.
(v) b and d are all 1; and a and c are all 0.
(vi) b is 1; and a, c and d are all 0.

$R^2$, $R^3$, $R^4$, $R^5$ and $R^7$ are independently of each other selected from the group consisting of H, F, methyl, ethyl, methyl wherein one or more hydrogen is replaced by fluorine, ethyl wherein one or more hydrogen is replaced by fluorine, and two or three neighboring groups of $R^2$, $R^3$, $R^4$, $R^5$ and $R^7$ may together form an aliphatic or aromatic ring system having a total of from 6 to 24 aromatic ring atoms. Exemplary aliphatic ring systems may be selected from the group consisting of cyclopentane, cyclohexane, cycloheptane, cyclopoctane, cyclononane, and cyclodecane. Cyclopentane and cyclohexane are preferred examples of aliphatic ring systems. Exemplary aromatic ring systems may be selected from the group consisting of benzene, pyridine, pyridazine, pyrimidine, pyrazine, 1,2,3-triazine, 1,2,4-triazine, napthalene, quinoline, isoquinoline, cinnoline, quinazoline, quinoxaline, phthalazine, 1,2,3-triazine, 1,2,4-triazine, anthracene, phenantrene, acridine, phenanthridine, and phenazine. Benzene and pyridine are preferred examples of aromatic ring systems.

In a preferred moiety of general formula (I) $X^1$ is C—$R^5$, and $R^2$ and $R^5$ together may be —(C—$R^9$)$_3$—, with $R^9$ as defined below.

Other preferred moieties of general formula (I) may be selected from one of the following:
(i) $R^3$ and $R^4$ together may be —(C—$R^9$)$_4$—, with $R^9$ as defined below; or
(ii) $X^4$ is N—$R^7$ and $R^3$ and $R^7$ together may be selected from the group consisting of —(C—$R^9$)$_3$—, —(C—$R^9$)$_2$— and —(C—$R^9$)—, with $R^9$ as defined below; or
(iii) $X^4$ is N—$R^7$ and $R^3$, $R^4$ and $R^7$ together may be —(C—$R^9$)$_2$—N—(C—$R^9$)$_3$—, with $R^9$ as defined below, or
(iv) $X^3$ is N—$R^6$, or
(v) $X^2$ is —C(=O)—, $X^3$ is N—$R^6$ and $X^4$ is —C(=O)—, optionally in combination with $X^1$ being C—$R^5$, and $R^2$ and $R^5$ together being —(C—$R^9$)$_3$—, with $R^9$ as defined below.

$R^9$ may be selected from the group consisting of H, F, methyl, ethyl, methyl wherein one or more hydrogen is replaced by fluorine, ethyl wherein one or more hydrogen is replaced by fluorine, or two neighboring groups $R^9$ may together form an aromatic ring system having from 6 to 24 aromatic ring atoms, which may in turn be substituted by $R^{10}$ being selected from the group consisting of H, F, ethyl, methyl wherein one or more hydrogen is replaced by fluorine, ethyl wherein one or more hydrogen is replaced by fluorine, —$X^a$—, —$X^a$—$X^b$—, —C(=$X^a$)—$X^b$—, —$X^a$O$_3$H, —$X^a$—$X^b$O$_3$H, —PO$_2$H$_2$ and —PO$_3$H$_2$, with $X^a$ and $X^b$ being independently of each S or Se.

Specific examples of moieties of general formula (I) may be selected from the group consisting of formulae (I-A) to (I-D)

(I-A)

(I-B)

(I-C)

(I-D)

Of these, formulae (I-A) and (I-B) are preferred.

Specific examples of formula (I-A) may be selected from the group consisting of the following formulae (I-A-1) to (I-A-8)

(I-A-1)

-continued (I-A-2)

(I-A-3)

(I-A-4)

(I-A-5)

(I-A-6)

-continued

(I-A-7)

(I-A-8)

Specific examples of formula (I-B) may be selected from the group consisting of the following formulae (I-B-1) to (I-B-7)

(I-B-1)

(I-B-2)

(I-B-3)

(I-B-4)

(I-B-5)

(I-B-6)

(I-B-7)

The present self-assembled monolayer may also comprise more than one moiety of the present invention or may also comprise a compound known to form self-assembled monolayers, such as the compounds disclosed by Boudinet et al. in Organic Electronics 11 (2010) 227-237 or by M. Malicki et al. in Langmuir 2009, 25(14), 7967-7975.

Preferably the self-assembled monolayers of the present invention may have a thickness (measured perpendicular to the surface of such layer) from 1 to 10, more preferably from 1 to 5, even more preferably from 1 to 3, and still even more preferably from 1 to 2 molecular layers. Most preferably said thickness is one molecular layer.

The resulting self-assembled monolayers have been found useful for the modification of surface properties of metal or metal oxide surfaces. Such metal or metal oxide surfaces may for example be electrodes in electronic devices. Specific examples of such electrodes in electronic devices may for example be the source and drain electrodes in an organic field effect transistor.

The types of metal and metal oxide that may be used in the present invention are not particularly limited and may also include alloys and any blend of metals, any blend of metal oxides as well as any blend of metals and metal oxides.

Exemplary metals, which are particularly suitable as electrodes in electronic devices, particularly in organic electronic devices, may be selected from the group consisting of gold, silver, copper, aluminum, nickel, palladium, platinum, titanium and any blend thereof. Of these gold and silver are particularly preferred. Silver is most preferred.

Exemplary alloys, which are particularly suitable as electrodes in electronic devices, particularly in organic electronic devices, include stainless steel (e.g., 332 stainless steel, 316 stainless steel), alloys of gold, alloys of silver, alloys of copper, alloys of aluminum, alloys of nickel, alloys of palladium, alloys of platinum, and alloys of titanium.

Exemplary electrically conducting metal oxides include indium tin oxide, fluorinated tin oxide, tin oxide, zinc oxide and any blend thereof.

Thus, the present application also relates to metal or metal oxide surfaces covered by a self-assembled monolayer comprising a moiety of the present invention. The term "covered" is to mean that at least 10%, or 20% or 30%, or 40%, or 50%, or 60%, or 70% or 80% or 90% or 95% or 97% or 99% of such metal or metal oxide surface is covered by said self-assembled monolayer. In other words, the metal or metal oxide surface is in contact with said self-assembled monolayer. Preferably said contact is a direct physical contact. Expressed differently, it is preferred that the present self-assembled monolayer is directly adjacent to the metal or metal oxide surface.

For the purposes of the present application the term "metal" may also denote a blend of one or more metals and one or more metal oxides wherein the content of the one or more metals is more than 50 wt %, relative to the total weight of said blend. Analogously the term "metal oxide" may also denote a blend of one or more metals and one or more metal oxides wherein the content of the one or more metal oxides is more than 50 wt %, relative to the total weight of said blend.

Without wishing to be bound by theory it is believed that the moieties of general formula (I) which are comprised in said self-assembled monolayer are oriented in such a way that functional group $X^5$ is in proximity of the metal or metal oxide surface while the remainder faces away from the metal or metal oxide surface. It is believed that such orientation results in improved surface properties, such as improved charge injection and charge transport, on the side of the self-assembled monolayer facing away from the metal or metal oxide surface. Furthermore, the substituents allow controlling the wettability of such self-assembled monolayer and thus help in the deposition of further layers thereon.

Furthermore, the present application also relates to electronic devices, preferably to organic electronic devices, comprising a metal or metal oxide surface covered by said self-assembled monolayer of the present invention. For example, the present application relates to electronic devices, preferably to organic electronic devices, comprising a metal or metal oxide electrode covered by a self-assembled monolayer of the present invention.

The electronic devices of the present invention may for example be selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (OSC), photodiodes, laser diodes, photoconductors, organic photodetectors (OPD), electrophotographic devices, electrophotographic recording devices, organic memory devices, sensor devices, biosensors, biochips, security markings, security devices, and components or devices for detecting and discriminating DNA sequences.

Preferably said electronic devices are selected from the group consisting of organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes, photoconductors and photodetectors.

Such electronic devices are well known to the skilled person and will in the following be illustrated using organic field effect transistors (OFETs). An organic field effect transistor may comprise a gate electrode, an insulating (or gate insulator) layer, a source electrode, a drain electrode and an organic semiconducting channel connecting the source and drain electrodes, wherein any or all of the electrodes—if comprising a metal or a metal oxide or both—may be in contact with a self-assembled monolayer in accordance with the present invention. Other features of the OFET are well known to those skilled in the art.

OFETs where an organic semiconducting material is arranged as a thin film between a gate dielectric and a drain and a source electrode, are generally known and are described for example in U.S. Pat. Nos. 5,892,244, 5,998,804 and 6,723,394.

In an OFET device gate, source and drain electrodes and an insulating layer and a semiconducting layer may be arranged in any sequence, provided that the source electrode and the drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a self-assembled monolayer in accordance with the present invention,
  a semiconducting layer,
  one or more gate insulator layers, and
  optionally a substrate,
wherein at least one of the electrodes comprises a metal or a metal oxide. Preferably said at least one of the electrodes comprising a metal or a metal oxide is covered by the self-assembled monolayer.

The OFET device can be a top gate device or a bottom gate device. Suitable structures and manufacturing methods of an OFET device are known to the skilled person and are described in the literature, for example in US 2007/0102696 A1.

Figure 1:
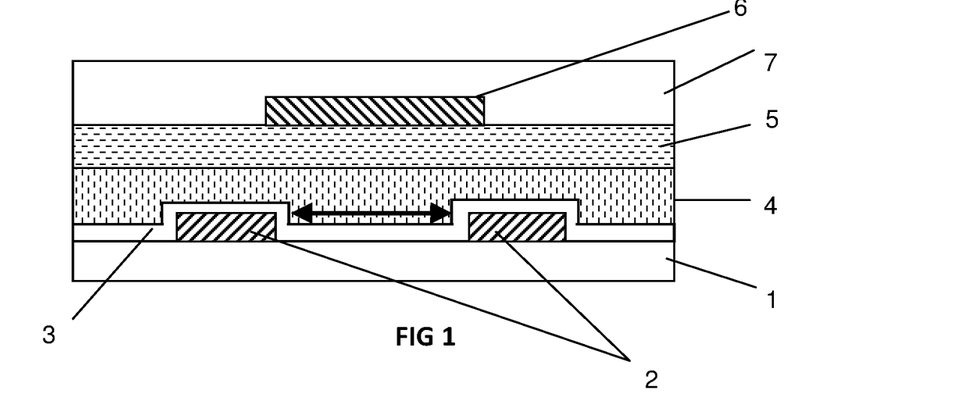
FIG. 1 shows a schematic exemplary representation of a top gate organic field effect transistor.

FIG. 1 shows a schematic representation of a typical top gate OFET according to the present invention, including source (S) and drain (D) electrodes (2) provided on a substrate (1), a self-assembled monolayer (3) of a moiety of general formula (I) of the present invention provided on the S/D electrodes, a layer of organic semiconducting material (4) provided on the S/D electrodes and the self-assembled monolayer (3), a layer of dielectric material (5) as gate insulator layer provided on the organic semiconducting layer (4), a gate electrode (6) provided on the gate insulator layer (5), and an optional passivation or protection layer (7) provided on the gate electrode (6) to shield it from further layers or devices that may be provided later or to protect it from environmental influence. The area between the source and drain electrodes (2), indicated by the double arrow, is the channel area.

Figure 2:
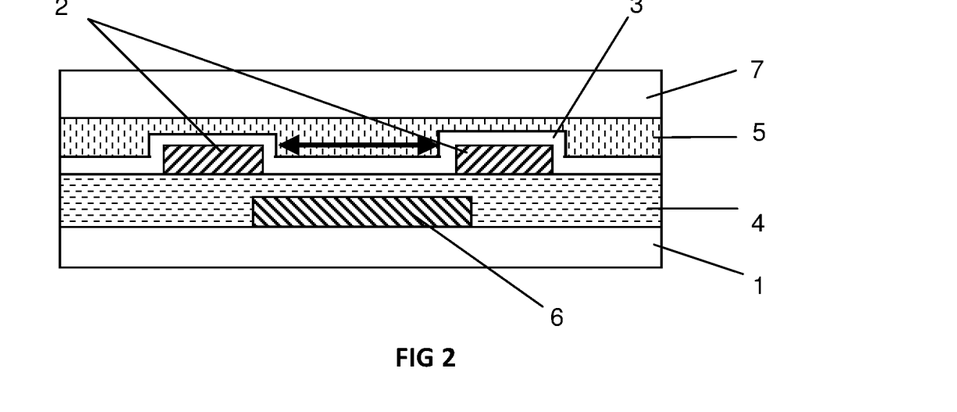
FIG. 2 shows a schematic exemplary representation of a bottom gate organic field effect transistor.

FIG. 2 shows a schematic representation of a typical bottom gate-bottom contact OFET according to the present invention, including a gate electrode (6) provided on a substrate (1), a layer of dielectric material (5) (gate insulator layer) provided on the gate electrode (4), source (S) and drain (D) electrodes (2) provided on the gate insulator layer (6), a self-assembled monolayer (3) of a moiety of general formula (I) of the present invention provided on the S/D electrodes, a layer of an organic semiconducting material (4) provided on the S/D electrodes and the self-assembled monolayer (3), and an optional protection or passivation layer (7) provided on the organic semiconducting layer (4) to shield it from further layers or devices that may be later provided or protect it from environmental influences.

Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a dielectric constant from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the electronic device in accordance with the present invention may be an OLED. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science,* 1998, 279, 835-837.

The electronic devices of the present invention may be produced by standard methods well known to the skilled person. Liquid coating of devices is more desirable than vacuum deposition techniques. Solution deposition methods are especially preferred. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

The organic semiconducting materials and methods for applying the organic semiconductor layer can be selected from standard materials and methods known to the person skilled in the art, and are described in the literature.

The organic semiconducting material may for example be an n-type or p-type organic semiconductor, which can be deposited by vacuum or vapor deposition, or preferably deposited from a solution. Preferably organic semiconducting materials are used which have a FET mobility of greater than $10^{-5}$ cm$^2$V$^{-1}$s$^{-1}$.

The organic semiconducting materials are for example used as the active channel material in an organic field effect transistor or a layer element of an organic rectifying diode. Organic semiconducting materials that may be deposited by liquid coating to allow ambient processing are preferred. Organic semiconducting materials are preferably spray-, dip-, web- or spin-coated or deposited by any liquid coating technique. Ink-jet deposition is also suitable. The organic semiconducting material may optionally be vacuum or vapor deposited.

The semiconducting channel may also be a composite of two or more of the same types of semiconductors. Furthermore, a p-type channel material may for example be mixed with n-type materials for the effect of doping the layer. Multilayer semiconductor layers may also be used. For example the semiconductor may be intrinsic near the insulator interface and a highly doped region can additionally be coated next to the intrinsic layer.

The organic semiconducting material may be a monomeric compound (also referred to as "small molecule", as compared to a polymer or macromolecule) or a polymeric compound, or a mixture, dispersion or blend containing one or more compounds selected from either or both of monomeric and polymeric compounds.

In case of monomeric materials, the organic semiconducting material is preferably a conjugated aromatic molecule, and contains preferably at least three aromatic rings. Preferred monomeric organic semiconducting materials are selected from the group consisting of conjugated aromatic molecules containing 5-, 6- or 7-membered aromatic rings, more preferably containing 5- or 6-membered aromatic rings.

In these conjugated aromatic molecules, each of the aromatic rings optionally contains one or more hetero atoms selected from Se, Te, P, Si, B, As, N, O or S, preferably from N, O or S. Additionally or alternatively, in these conjugated aromatic molecules, each of the aromatic rings is optionally substituted with alkyl, alkoxy, polyalkoxy, thioalkyl, acyl, aryl or substituted aryl groups, halogen, particularly fluorine, cyano, nitro or an optionally substituted secondary or tertiary alkylamine or arylamine represented by —N(R')(R"), where R' and R" are independently of each other selected from the group consisting of H, an optionally substituted alkyl group, or an optionally substituted aryl, alkoxy or polyalkoxy group. Where R' and R" is an alkyl or aryl group, these are optionally fluorinated.

In these conjugated aromatic molecules, the aromatic rings are optionally fused or are optionally linked to each other by a conjugated linking group such as —C(T$^1$)=C(T$^2$)—, —C≡C—, —N(R''')—, —N=N—, —C(R''')=N—, —N=C(R''')—, wherein T$^1$ and T$^2$ are independently of each other selected from the group consisting of H, Cl, F, —CN or a C$_1$-C$_{10}$ alkyl group, preferably a C$_1$-C$_4$ alkyl group; R''' is selected from the group consisting of H, an optionally substituted C$_1$-C$_{20}$ alkyl group or an optionally substituted C$_4$-C$_{30}$ aryl group. Where R''' is an alkyl or aryl group, these may optionally be fluorinated.

Further preferred organic semiconducting materials that can be used in this invention include compounds, oligomers and derivatives of compounds selected from the group consisting of conjugated hydrocarbon polymers such as polyacene, polyphenylene, poly(phenylene vinylene), polyfluorene including oligomers of those conjugated hydrocarbon polymers; condensed aromatic hydrocarbons such as tetracene, chrysene, pentacene, pyrene, perylene, coronene, or soluble, substituted derivatives of these; oligomeric para substituted phenylenes such as p-quaterphenyl (p-4P), p-quinquephenyl (p-5P), p-sexiphenyl (p-6P), or soluble substituted derivatives of these; conjugated heterocyclic polymers such as poly(3-substituted thiophene), poly(3,4-bisubstituted thiophene), optionally substituted polythieno[2,3-b]thiophene, optionally substituted polythieno[3,2-b]thiophene, poly(3-substituted selenophene), polybenzothiophene, polyisothianapthene, poly(N-substituted pyrrole), poly(3-substituted pyrrole), poly(3,4-bisubstituted pyrrole), polyfuran, polypyridine, poly-1,3,4-oxadiazoles, polyisothianaphthene, poly(N-substituted aniline), poly(2-substituted aniline), poly(3-substituted aniline), poly(2,3-bisubstituted aniline), polyazulene, polypyrene; pyrazoline compounds; polyselenophene; polybenzofuran; polyindole; polypyridazine; benzidine compounds; stilbene compounds; triazines; substituted metallo- or metal-free porphines, phthalocyanines, fluorophthalocyanines, naphthalocyanines or fluoronaphthalocyanines; C$_{60}$ and C$_{70}$ fullerenes; N,N'-dialkyl, substituted dialkyl, diaryl or substituted diaryl-1,4,5,8-naphthalenetetracarboxylic diimide and fluoro derivatives; N,N'-dialkyl, substituted dialkyl, diaryl or substituted diaryl 3,4,9,10-perylenetetracarboxylicdiimide; bathophenanthroline; diphenoquinones; 1,3,4-oxadiazoles; 11, 11, 12, 12-tetracyanonaptho-2,6-quinodimethane; a, a' bis(dithieno[3,2-b2',3'-d]thiophene); 2,8-dialkyl, substituted dialkyl, diaryl or dialkynyl anthradithiophene; 2,2'-bibenzo[1,2-b:4,5-b']dithiophene. Preferred compounds are those from the above list and derivatives thereof which are soluble in organic solvents.

Especially preferred organic semiconducting materials are selected from the group consisting of polymers and copolymers comprising one or more repeating units selected from thiophene-2,5-diyl, 3-substituted thiophene-2,5-diyl, selenophene-2,5-diyl, 3-substituted selenophene-2,5-diyl, optionally substituted thieno[2,3-b]thiophene-2,5-diyl, optionally substituted thieno[3,2-b]thiophene-2,5-diyl, optionally substituted 2,2'-bithiophene-5,5'-diyl, optionally substituted 2,2'-biselenophene-5,5'-diyl.

Further preferred organic semiconducting materials are selected from the group consisting of substituted oligoacenes such as pentacene, tetracene or anthracene, or heterocyclic derivatives thereof, like 6,13-bis(trialkylsilylethynyl) pentacenes or 5,11-bis(trialkylsilylethynyl) anthradithiophenes, as disclosed for example in U.S. Pat. No. 6,690,029, WO 2005/055248 A1 or U.S. Pat. No. 7,385,221.

In another preferred embodiment of the present invention the organic semiconducting layer of the electronic device comprises one or more organic binders to adjust the rheological properties as described for example in WO 2005/055248 A1, in particular an organic binder which has a low permittivity, c, at 1,000 Hz of 3.3 or less.

The binder is selected for example from poly(alpha-methylstyrene), polyvinylcinnamate, poly(4-vinylbiphenyl) or poly(4-methylstyrene, or blends thereof. The binder may also be a semiconducting binder selected for example from polyarylamines, polyfluorenes, polythiophenes, polyspirobifluorenes, substituted polyvinylenephenylenes, polycarbazoles or polystilbenes, or copolymers thereof.

A preferred dielectric material for use in the present invention preferably comprises a material with a low permittivity of between 1.5 and 3.3 at 1000 Hz. An example of such a material is Cytop™ 809 M commercially available from Asahi Glass.

The transistor device according to the present invention may also be a complementary organic thin film transistor (CTFT) comprising both a p-type semiconducting channel and an n-type semiconducting channel.

The self-assembled monolayer of the present invention are not only useful in organic field effect transistors, but can also be used in any organic electronic device comprising a metal electrode or a metal oxide electrode, like for example organic light emitting devices (OLEDs) or organic photovoltaic (OPV) devices. The skilled person can easily make the required modifications in order to use it in other organic electronic devices.

For example, the present can also be applied to an electrode in an organic photovoltaic device, like for example in a bulk heterojunction (BHJ) solar cell. The organic photovoltaic device can be of any type known from the literature [see e.g. Waldauf et al., Appl. Phys. Lett. 89, 233517 (2006)].

A preferred organic photovoltaic device according to the present invention comprises:
- a low work function electrode (for example a metal, such as aluminum), and a high work function electrode (for example indium tin oxide, frequently referred to as "ITO"), one of which is transparent,
- a layer (also referred to as "active layer") comprising a hole transporting material and an electron transporting material, preferably selected from organic semiconducting materials, situated between the low work function electrode and the high work function electrode; the active layer can exist for example as a bilayer or two distinct layers or blend or mixture of p-type and n-type semiconductor, forming a bulk heterjunction (BHJ) (see for example Coakley, K. M. and McGehee, M. D. Chem. Mater. 2004, 16, 4533),
- an optional coating (for example of LiF) on the side of the low work function electrode facing the active layer, to provide an ohmic contact for electrons, wherein at least one of the electrodes, preferably the high work function electrode, is covered with a self-assembled monolayer in accordance with the present invention.

Another preferred organic photovoltaic device according to the present invention is an inverted organic photovoltaic device that comprises:
- a low work function electrode (for example a metal, such as gold), and a high work function electrode (for example ITO), one of which is transparent,
- a layer (also referred to as "active layer") comprising a hole transporting material and an electron transporting material, preferably selected from organic semiconducting materials, situated between the low work function electrode and the high work function electrode; the active layer can exist for example as a bilayer or two distinct layers or blend or mixture of p-type and n-type semiconductor, forming a BHJ,
- an optional coating (for example of $TiO_x$) on the side of the high work function electrode facing the active layer, to provide an ohmic contact for holes, wherein at least one of the electrodes, preferably the high work function electrode, is covered with a self-assembled monolayer in accordance with the present invention.

Thus, in the organic photovoltaic devices of the present invention preferably at least one of the electrodes, preferably the high work function electrode, is covered, on its surface facing the active layer, by a layer comprising a moiety in accordance with the present invention. Said layer is advantageously applied by process according to the present invention as described above and below.

The organic photovoltaic devices in accordance with the present invent invention typically comprise a p-type (electron donor) semiconductor and an n-type (electron acceptor) semiconductor. The p-type semiconductor is for example a polymer like poly(3-alkyl-thiophene) (P3AT), preferably poly(3-hexylthiophene) (P3HT), or alternatively another selected from the groups of preferred polymeric and monomeric organic semiconducting material as listed above. The n-type semiconductor can be an inorganic material such as zinc oxide or cadmium selenide, or an organic material such as a fullerene derivate, for example (6,6)—phenyl-butyric acid methyl ester derivatized methano $C_{60}$ fullerene, also known as "PCBM" or "$C_{60}PCBM$", as disclosed for example in G. Yu, J. Gao, J. C. Hummelen, F. Wudl, A. J. Heeger, Science 1995, Vol. 270, p. 1789 ff and having the structure shown below, or an structural analogous compound with e.g. a $C_{70}$ fullerene group ($C_{70}PCBM$), or a polymer (see for example Coakley, K. M. and McGehee, M. D. Chem. Mater. 2004, 16, 4533).

$C_{60}PCBM$

A preferred material of this type is a blend or mixture of a polymer like P3HT or another polymer selected from the groups listed above, with a $C_{60}$ or $C_{70}$ fullerene or modified fullerene like PCBM. Preferably the ratio polymer:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently organic photovoltaic device performance.

The present self-assembled monolayer may be prepared by applying a compound (in the following denoted "precursor compound") comprising the moiety of formula (I) to a metal surface or a metal oxide surface, which is supported on a substrate. Preferably in said precursor compound $R^1$ and—if present—$R^6$ are independently of each other selected from the group consisting of H, F, methyl, ethyl, methyl wherein one or more hydrogen is replaced by fluorine, ethyl wherein one or more hydrogen is replaced by fluorine, and —$(C\equiv C)_a$—$(Ar^1)_b$—$(C\equiv C)_c$—$(R^8)_d$—$X^5$—H with $Ar^1$, $R^8$, $X^5$, a, b, c and d as defined above, provided that if $X^3$ is N—$R^6$ $R^1$ and $R^6$ are not both —$(C\equiv C)_a$—$(Ar^1)_b$—$(C\equiv C)_c$—$(R^8)_d$—$X^5$—H.

Alternatively said precursor compound may also comprise two moieties, i.e. a first and a second moiety, of formula (I) linked by —$(C\equiv C)_a$—$(Ar^1)_b$—$(C\equiv C)_c$—$(R^8)_d$—S—S—$(R^8)_d$—$(C\equiv C)_c$—$(Ar^1)_b$—$(C\equiv C)_a$— with $Ar^1$, $R^8$, $X^5$, a, b, c and d as defined above. This means that $R^1$ on the first moiety may be linked to $R^1$ on the second moiety, or $R^1$ on the first moiety may be linked to $R^6$ on the second moiety, $R^6$ on the first moiety may be linked to $R^6$ on the second moiety of such a precursor compound comprising two moieties of formula (I).

The process of the present invention therefore provides for a process for the preparation of a self-assembled monolayer on a metal surface or a metal oxide surface, and ultimately the production of electronic devices, preferably organic electronic devices, comprising such self-assembled monolayer, said process comprising the steps of
(a) providing a metal surface or a metal oxide surface, and
(c) applying one or more precursor compounds as defined above to said metal surface or metal oxide surface,
thus obtaining a self-assembled monolayer in accordance with the present invention on said metal surface or metal oxide surface.

The metal surface or the metal oxide surface of step (a) may be the surface of an electrode. In a organic field effect transistor said electrode may for example be the source electrode or the drain electrode or both. Preferably, such electrodes are provided on a supporting layer. Examples of suitable supporting layers or substrates, as they may be referred to in the context of electronic devices, are given below.

The above-defined precursor compound may be applied onto the metal surface or the metal oxide surface by vacuum or vapor deposition methods or by liquid coating methods. Exemplary deposition methods include physical vapor deposition (PVD), chemical vapor deposition (CVD), sublimation or liquid coating methods. Liquid coating methods are preferred. Particularly preferred are solvent-based liquid coating methods.

In solvent-based liquid coating a formulation, which comprises the above-defined precursor compound and a solvent, is deposited onto the metal surface or the metal oxide surface. Optionally, following deposition the solvent may be at least partially evaporated. Preferred solvent-based liquid coating methods include, without limitation, dip coating, spin coating, ink jet printing, letter-press printing, screen printing, doctor blade coating, roller printing, reverse-roller printing, offset lithography printing, flexographic printing, gravure printing, web printing, spray coating, brush coating and pad printing.

In the following, the step of applying the above-defined precursor compound to an electrode so as to obtain the self-assembled monolayer of the present invention may also be referred to as "SAM treatment".

Suitable solvents for use in the step (a) of the above process may be selected from the group consisting of alcohols, ethers, ketones, aromatic hydrocarbons and any mixture of any of these. Suitable alcohols may for example be selected from the group consisting of methanol, ethanol, isopropanol and n-propanol. Suitable ethers may have a linear or a cyclic structure and may for example be selected from the group consisting of diethylether, tetrahydrofuran (THF), butyl phenyl ether, methyl ethyl ether and 4-methylanisole. Suitable ketones may for example be selected from the group consisting of acetone, 2-heptanone and cyclohexanone. Suitable aromatic hydrocarbons may for example be selected from the group consisting of toluene, mesitylene, o-xylene, m-xylene, p-xylene, cyclohexylbenzene and halogenated aromatic hydrocarbons. Examples of such halogenated aromatic hydrocarbons are chlorobenzene, dichlorobenzene and trichlorobenzene as well as any mixture of any of these.

Preferably the above-defined precursor compounds are present in the formulation or solution in from 0.01 wt % to 10 wt %, preferably from 0.01 wt % to 5 wt %, and most preferably from 0.05 wt % to 2 wt %, with wt % being relative to the total weight of the formulation or solution.

The metal or metal oxide may be applied to the substrate by any of the conventional methods. The methods may for example be selected from vacuum deposition, vapor deposition and liquid coating. Exemplary deposition methods include physical vapor deposition (PVD), chemical vapor deposition (CVD), sublimation or liquid coating methods. Such methods form part of the general knowledge in the field and are well known to the skilled person.

Before the SAM treatment, i.e. the formation of the self-assembled monolayer, the metal or metal oxide surface is preferably subjected to a washing step. A preferred washing step comprises an acidic washing with a acid or a blend of acids, said acids being organic or inorganic acids. Examples of suitable acids are acetic acid, citric acid or hydrochloric acid. Alternatively the metal or metal oxide surface may be subjected to a plasma treatment step.

In a preferred embodiment, the washing step and the SAM treatment are combined into a single step. For example, this combined step may be carried out by applying a formulation in accordance with the present invention to the metal or metal oxide surface, said formulation comprising a precursor compound as defined above and an acid as defined above.

Alternatively the washing step and the SAM treatment may be carried out sequentially in two separate steps.

The soaking time, i.e. the time during which the formulation is applied to the metal or metal oxide surface, is preferably at least 5 s and at most 72 h.

In the preparation of the other layers of the electronic devices, preferably the organic electronic devices, of the present invention standard methods may be used to deposit the various layers and materials as described above.

Preferably the deposition of individual functional layers in the preparation of the present electronic devices, such as for example the organic semiconducting layer or the insulator layer, is carried out using solution processing techniques. This can be done for example by applying a formulation, preferably a solution, comprising the organic semiconducting material or the dielectric material and further comprising one or more organic solvents, onto the previously deposited layer, followed by evaporation of the solvent(s). Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating, or pad printing. Very preferred solution deposition techniques are spin coating, flexographic printing and inkjet printing.

In an OFET device according to the present invention, the dielectric material for the gate insulator layer is preferably an organic material. It is preferred that the dielectric layer is solution coated which allows ambient processing, but could also be deposited by various vacuum deposition techniques. When the dielectric is being patterned, it may perform the function of interlayer insulation or act as gate insulator for an OFET. Preferred deposition techniques include, without limitation, dip coating, spin coating, ink jet printing, letterpress printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared. Optionally, the dielectric material could be cross-linked or cured to achieve better resistance to solvents and/or structural integrity and/or to improve patterning (photolithography). Preferred gate insulators are those that provide a low permittivity interface to the organic semiconductor.

Suitable solvents are selected from solvents including but not limited to hydrocarbon solvents, aromatic solvents, cycloaliphatic cyclic ethers, cyclic ethers, acetates, esters, lactones, ketones, amides, cyclic carbonates or multi-component mixtures of the above. Examples of preferred solvents include cyclohexanone, mesitylene, xylene, 2-heptanone, toluene, tetrahydrofuran, MEK (methyl ethyl ketone), MAK (2-heptanone), cyclohexanone, 4-methylanisole, butyl-phenyl ether and cyclohexylbenzene, very preferably MAK, butyl phenyl ether or cyclohexylbenzene.

The total concentration of the respective functional material (organic semiconducting material or gate dielectric material) in the formulation is preferably from 0.1 to 30 wt %, preferably from 0.1 to 5 wt %, relative to the total weight of the formulation (i.e. functional material(s) and solvent(s)). In particular organic ketone solvents with a high boiling point are advantageous for use in solutions for inkjet and flexographic printing.

When spin coating is used as deposition method, the OSC or dielectric material is spun for example between 1000 and 2000 rpm for a period of for example 30 seconds to give a layer with a typical layer thickness between 0.5 and 1.5 μm. After spin coating the film can be heated at an elevated temperature to remove all residual volatile solvents.

Optionally the dielectric material layer is annealed after exposure to radiation, for example at a temperature from 70° C. to 130° C., for example for a period of from 1 to 30 minutes, preferably from 1 to 10 minutes. The annealing step at elevated temperature can be used to complete the cross-linking reaction that was induced by the exposure of the cross-linkable groups of the dielectric material to photoradiation.

All process steps described above and below can be carried out using known techniques and standard equipment which are described in prior art and are well-known to the skilled person. For example, in the photoirradiation step a commercially available UV lamp and photomask can be used, and the annealing step can be carried out in an oven or on a hot plate.

The thickness of a functional layer (organic semiconducting layer or dielectric layer) in an electronic device according to the present invention is preferably from 1 nm (in case of a monolayer) to 10 μm, very preferably from 1 nm to 1 μm, most preferably from 5 nm to 500 nm.

Various substrates may be used for the fabrication of organic electronic devices, for example silicon wafers, glass or plastics, plastics materials being preferred, examples including alkyd resins, allyl esters, benzocyclobutenes, butadiene-styrene, cellulose, cellulose acetate, epoxide, epoxy polymers, ethylene-chlorotrifluoro ethylene, ethylene-tetrafluoroethylene, fibre glass enhanced plastic, fluorocarbon polymers, hexafluoropropylenevinylidene-fluoride copolymer, high density polyethylene, parylene, polyamide, polyimide, polyaramid, polydimethylsiloxane, polyethersulphone, poly-ethylene, polyethylenenaphthalate, polyethyleneterephthalate, polyketone, polymethylmethacrylate, polypropylene, polystyrene, polysulphone, polytetrafluoroethylene, polyurethanes, polyvinylchloride, silicone rubbers, and silicones.

Preferred substrate materials are polyethyleneterephthalate, polyimide, and polyethylenenaphthalate. The substrate may be any plastic material, metal or glass coated with the above materials. The substrate should preferably be homogeneous to ensure good pattern definition. The substrate may also be uniformly pre-aligned by extruding, stretching, rubbing or by photochemical techniques to induce the orientation of the organic semiconductor in order to enhance carrier mobility.

A preferred process for the manufacture of organic electronic devices in accordance with the present invention comprises the steps of (a) depositing a metal or a metal oxide to form a source electrode and a drain electrode on a substrate, (b) optionally washing the surfaces of said source electrode and said drain electrode; and (c) applying one or more precursor compounds as defined above to said source electrode and said drain electrode, thus obtaining a self-assembled monolayer on the surfaces of said source electrode and said drain electrode;

(d) depositing a organic semiconducting material onto the source and drain electrodes and the self-assembled monolayer, thus forming an organic semiconducting layer.

Optionally steps (b) and (c) may be combined into a single step.

Optionally in step (c) the application of the one or more precursor compounds as defined above may be followed by at least partial removal of any solvents present or by annealing the self-assembled monolayer or by both.

Optionally in step (d) the deposition of the organic semiconducting material may be followed by at least partial removal of any solvents present or by annealing the organic semiconducting material or by both.

In addition to above steps (a) to (d) the process for manufacturing the organic electronic devices in accordance with the present invention may further comprise the following steps:

(e) depositing a gate insulator material onto said organic semiconducting layer, thereby forming a gate insulator layer;

(f) depositing a gate electrode onto said gate insulator layer; and (g) optionally depositing a passivation layer onto said gate electrode.

For the preparation of a top gate transistor, the source and drain electrodes are usually applied onto a substrate as defined above, followed by the deposition thereon of a self-assembled monolayer in accordance with the present invention. A gate insulator can then be applied on the organic semiconducting layer, onto which in turn a gate electrode may be deposited.

For the preparation of a bottom gate transistor, the gate electrode is usually applied to a substrate. The gate insulator layer is then formed on top of said gate electrode. Source and drain electrodes are then applied to the gate insulator, followed by the deposition thereon of a self-assembled monolayer in accordance with the present invention.

Depending upon the type of electronic device to be manufactured and the respective architecture, the above process for manufacturing organic electronic devices may be modified, for example by including the formation of additional layers, which are different from the ones included in any of above steps (a) to (g).

Process conditions may also be adapted without difficulty to take account of the nature of the specific materials used in the production of the desired electronic device.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant c ("permittivity") refer to values taken at 20° C. and 1,000 Hz.

EXAMPLES

The advantages of the present invention are further illustrated by the following non-limiting examples.

If not otherwise indicated starting materials were purchased through commercial sources, such as for example Aldrich Chemicals.

Example 1

Synthesis

Step a

To 25 ml of degassed DMF (nitrogen flow; ca. 2 hours) were added 4-chloro-1,8-naphthalic anhydride 1 (1.17 g, 5.00 mmol, 1.00 eq) and sodium sulfide (780 mg, 10.0 mmol, 2.00 eq) and stirred at room temperature for 16 hours. The solution turned dark purple. Upon completion of the reaction 100 ml of water were added and acidified with concentrated hydrochloric acid until the solution achromatized. The forming of a yellow precipitate could be observed. The solids were collected by filtration and washed with distilled water. 1.05 g (92% crude yield) of a yellow solid 2 was collected as crude product. Due to poor solubilit the crude product was used without further purification in subsequent syntheses. Additionally due to the lack of solubility no satisfying NMR spectra could be obtained. The characterization occurred via mass spectrometry. The molar peak could be observed as well as suiting molecule fragments. No mentionable impurities could be detected in the mass spectra.

EI-MS: m/z=230.0 (Molecule; $C_{12}H_8O_3S$; calculated: 230.0)

186.0 (Fragment 1 (loss of $CO_2$); $C_6H_{11}OS$; calculated 186.0)

158.0 (Fragment 2 (Fragment 1—CO); $C_5H_{11}S$; calculated 158.0)

IR (solid, [cm$^{-1}$]): 3084 (w, broad); 1766 (s); 1731 (vs); 1585 (s); 1565 (s); 1328 (s); 1297 (s); 1223 (s); 1017 (vs); 774 (s); 745 (s); 417 (s).

Step b

To 40 ml of degassed (nitrogen flow; ca. 2 hours) ethanol (99% pure) was added crude 4-thio-1,8-naphthalic anhydride 2 (469 mg, 2.00 mmol, 1.00 eq) and n-octylamine (0.5 ml, 387 mg, 3.00 mmol, 1.50 eq). The reaction mixture changed color to a reddish orange and eventually to a dark purple. The reaction mixture was then stirred under reflux and nitrogen atmosphere for 16 hours. Upon completion of the reaction the flask was cooled to room temperature. The yellow precipitate was collected by filtration, washed with ethanol and dried under vacuum to yield 162 mg (23%) of pure product 3a (yellow solid).

$^1$H-NMR (300 MHz; CDCl$_3$): 8.63-8.58 (m, 2H); 8.35 (d, 3JH-H=7.7 Hz, 1H); 7.77-7.71 (m, 1H); 7.44 (d, 3JH-H=7.1 Hz, 1H); 4.12-4.17 (m, 2H); 1.71-1.61 (m, 2H7); 1.35-1.20 (m, 11H, aliphatic H+S-H); 0.82-0.78 (m, 3H).

$^{13}$C-NMR (75 MHz; CDCl$_3$): 163.7; 163.6; 139.4; 132.0; 130.9; 130.8); 130.6; 130.5; 128.9; 127.9; 123.6; 122.6); 40.7; 31.8; 29.3; 29.2; 28.1; 27.2; 22.7; 14.1.

IR (solid; [cm$^{-1}$]): 2922 (w, broad); 2853 (w); 1696 (m); 1652 (s); 1585 (m); 1342 (s); 1231 (m); 779 (m); 750 (m).

Alternative amines allow the introduction of different groups at the ring nitrogen atom as is shown in the following.

To 40 ml of degassed (nitrogen flow; ca. 2 hours) ethanol (99% pure) was added crude 4-thio-1,8-naphthalic anhydride 2 (460 mg, 2.00 mmol, 1.00 eq) and 2-ethylhexylamine (0.8 ml, 387 mg, 3.00 mmol, 1.50 eq). The reaction mixture immediately changed color to a dark purple. The reaction mixture was then stirred under reflux and nitrogen atmosphere for 16 hours. Upon completion of the reaction the flask was cooled to room temperature. The yellow precipitate was collected by filtration, washed with ethanol and dried under vacuum to yield 248 mg (36%) of pure product 3b as a yellow solid.

$^1$H-NMR (300 MHz; CDCl$_3$): 8.62 (d, 3JH-H=1.3 Hz, 1H); 8.60 (d, 3JH-H=2.9 Hz, 1H); 8.36 (d, 3JH-H=7.7 Hz, 1H); 7.77-7.72 (m, 1H); 7.45 (d, 3JH-H=7.7 Hz, 1H); 4.11-3.98 (m, 2H); 1.91-1.83 (m, 1H); 1.47 (bs, 1H); 1.35-1.18 (m, 8H); 0.89-0.76 (m, 6H).

$^{13}$C-NMR (75 MHz; CDCl$_3$): 164.1; 164.0; 139.4; 132.1; 130.9; 130.8; 130.5; 128.9; 127.9; 123.6; 122.6; 44.3; 38.0; 30.8; 28.7; 24.1; 23.1; 14.1; 10.7.

IR (solid; [cm$^{-1}$]): 2926 (w, broad); 2858 (w); 1700 (m); 1657 (s); 1585 (m); 1341 (m); 1229 (m); 780 (m); 749 (m).

Example 2

Synthesis of Jul-S-S-Jul

Step a

Julolidin hydrobromide 4 (6.35 g, 25.0 mmol, 1.00 eq) and ammonium thiocyanate (3.81 g, 50.0 mmol, 2.00 eq) were dissolved in glacial acetic acid and cooled to 10-15° C. Maintaining this temperature, bromine (1.3 ml, 4.00 g, 25.0 mmol, 1.00 eq) in 5 ml glacial acetic acid was added drop wise over a period of 20 minutes. The reaction mixture was poured into 800 ml of water whereupon a white precipitate formed. The solids were collected by filtration, washed with water and dried under vacuum. The white solid was recrystallized from ethanol to yield 3.90 g (67%) of pure product 5 as white needles.

$^1$H-NMR (300 MHz; CDCl$_3$): 6.98 (s, 2H); 3.20 (t, 3JH-H=5.6 Hz, 4H); 2.72 (t, 3JH-H=6.4 Hz, 4H); 2.02-1.93 (m, 4H).

Step b

Julolidin thiocyanate 5 (3.90 g, 16.9 mmol, 1.00 eq) was deposited in a round bottom flask. 3.80 g of potassium hydroxide (excess) was dissolved in 40 ml of preheated ethanol (ca. 50° C.). The warm solution was poured into the round bottom flask and stirred for 16 hours under ambient conditions. It could be seen that the furnished solid dissolved, subsequently followed by the formation of a brownish precipitate. The solid was collected by filtration, washed with ethanol and dried under vacuum. The crude product was purified by flash column chromatography (silica gel; petrol ether:ethyl acetate 10:1) yielding 1.99 g (58%) of a red, crystalline solid as pure product 6.

$^1$H-NMR (300 MHz; CDCl$_3$): 6.92 (s, 4H); 3.17 (t, 3JH-H=5.6 Hz, 8H); 2.70 (t, 3JH-H=6.5 Hz, 8H); 2.02-1.94 (m, 8H).

$^{13}$C-NMR (75 MHz; CDCl$_3$): 143.5; 132.3; 122.2; 121.6; 49.9; 27.6; 21.8.

EI-MS: m/z=408.2 (Molecule; C$_{24}$H$_{28}$N$_2$S$_2$; calculated 408.2)

204.1 (Fragment 1 (Monomer); C$_{12}$H$_{14}$NS; calculated: 204.1)

Example 3

Synthesis 1,8-Naphthalic anhydride 7 (1.00 g, 5.00 mmol, 1.00 eq) and 4-aminothiophenol (688 mg, 5.50 mmol, 1.10 eq) were dissolved in 20 ml pyridine and heated to reflux (120° C.) for 16 hours. The reaction mixture turned yellow solution at first. With increasing reaction time a yellow precipitate was formed. Upon completion of the reaction the solvent was removed under vacuum. The crude product was purified via flash column chromatography (silica gel; 2×ca. 10 cm). Ethyl acetate as eluent yielded a minor impure product fraction. Extraction of the previously washed column yielded 1.34 g (87%) of the pure product 8 as a white solid.

$^1$H-NMR (300 MHz; DMSO): 8.51 (d, 3JH-H=2.3 Hz, 2H); 8.49 (d, 3JH-H=1.4 Hz, 2H); 7.96-7.91 (m, 2H); 7.73 (d, 3JH-H=8.6 Hz, 2H); 7.46 (d, 3JH-H=8.6 Hz, 2H).

EI-MS: m/z=305.1 (molecule; $C_{18}H_{11}NO_2S$; calculated: 305.1)

608.1 (Disulfide-dimer; $C_{36}H_{22}N_2O_4S_2$; calculated: 608.1)

IR (solid, [cm$^{-1}$]): 1699 (m); 1660 (m); 1584 (m); 1492 (m); 1371 (m); 1350 (m); 1234 (m); 1187 (m); 1095 (m); 1016 (m); 810 (s); 780 (vs); 538 (m); 513 (m); 428 (m).

Example 4

Transistor Fabrication and Performance Measurement

Figure 3:
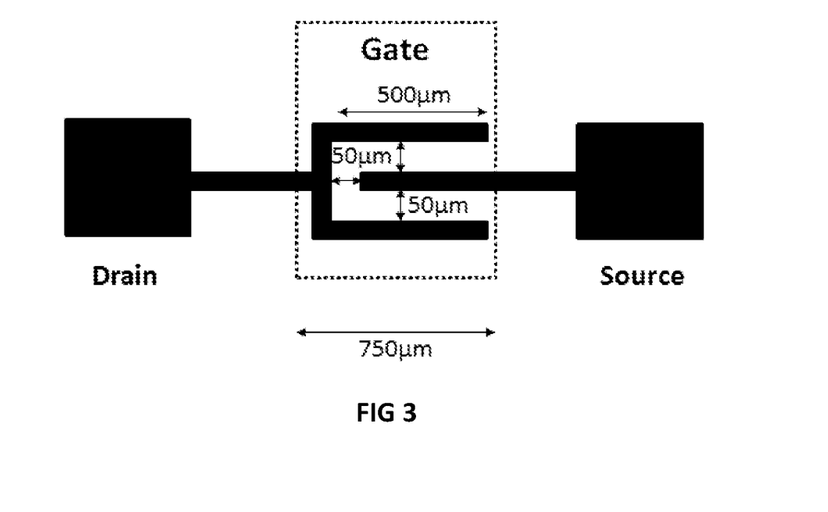
FIG. 3 is a schematic top view representation of the transistors of Example 4.

Bottom contact-top gate transistors having a channel width of 50 μm and a channel length of 1000 μm (see FIG. 3 for a schematic representation) were prepared on glass substrates. Ag electrodes were deposited onto the glass substrates by thermal evaporation, using lateral structuring with a shadow mask. The resulting structure was then immersed in a 1 mmol/l solution of the compound 6 in chlorobenzene, thus forming a self-assembled monolayer comprising Jul-S on the Ag surface. Subsequently a n-type semiconductor (ActivInk™ N2200 [P(NDI2OD-T2)]), Polyera Corporation, Skokie, Ill., USA) was spin-coated thereon from a 1 wt % chlorobenzene solution and annealed at 100° C. for 180 s. Then a dielectric layer was formed by spin coating an amorphous fluoropolymer (CYTOP™, ASAHI GLASS COMPANY) and annealed at 100° C. for 300 s. All spin coating steps were performed under nitrogen atmosphere in a glovebox. Finally a Ag gate electrode was deposited by thermal evaporation onto the dielectric layer.

ActivInk™ N2200

Thicknesses of the respective layers were determined with a Dektak profilometer with the following results:

TABLE 1

| | Thickness [nm] |
|---|---|
| Ag source and drain electrodes | 50 ± 5 |
| Semiconductor layer (ActivInk™ N2200) | 650 ± 50 |
| Dielectric layer (CYTOP™) | 80 ± 5 |

Figure 4:
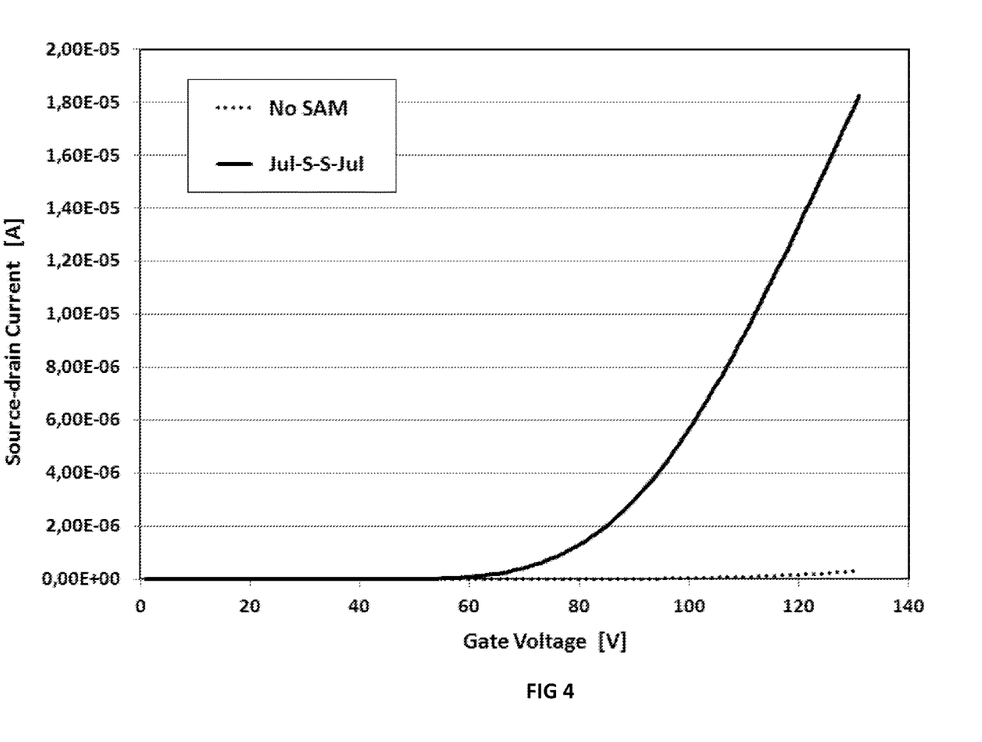
FIG. 4 shows the transfer characteristics of the transistors of Example 4.

Transistor transfer and output measurements were conducted in ambient atmosphere using an Agilent parameter analyzer. Transfer characteristics are shown in FIG. 4. Table 2 shows the respective mobilities, ratio between on- and off-current, the threshold voltage as well as the time for which the Ag-source and drain electrodes were immersed in the solution of the compound of Example 1.

TABLE 2

| Self-assembled monolayer Precursor compound | | No SAM (comparative) | Jul-S-S-Jul |
|---|---|---|---|
| $\mu_{sat}$ | [cm$^2$/Vs] | 0.01 | 0.15 |
| I on/off | | 5.6 · 10$^3$ | 4.0 · 10$^5$ |
| $V_{Threshold}$ | [V] | 60.1 | 33.7 |
| Immersion time | [h] | 0 | 5 |

The results clearly show the advantages of the present invention. In comparison to the devices comprising the untreated Ag source and drain electrodes the devices comprising a self-assembled monolayer in accordance with the present invention surprisingly show very much improved properties in respect of increased currents at a given voltage, improved ratio between on-current and off-current as well as a lower threshold voltage.

Example 5

Work Function and Contact Angle

To quantify the efficiency of the moieties of the present invention the respective work function (WF) of an Au surface and the contact angle of precursor compound 6 (Jul-S-S-Jul) was tested in comparison to precursor compounds benzylthiol ($C_6H_5$—$CH_2$—SH) and 4-methoxy-α-toluenethiol. The results are given in Table 3.

TABLE 3

| Precursor Compound | WF [eV] | Shift in WF [meV] | Contact angle (water) |
|---|---|---|---|
| Benzylthiol | 4.20 | −500 | 90° |
| 4-methoxy-α-toluenethiol | 4.20 | −500 | 75° |
| Jul-S-S-Jul | 4.20 | −500 | 45° |

It is shown that compound 6, a precursor compound in accordance with the present invention, shifts the work function and also has a significant influence on the contact angle. Thus, as evidenced by Jul-SH the compounds of the present application can give a different combination of impact on work function and wettability than conventional compounds as evidenced by the data for benzylthiol and 4-methoxy-a-toluenethiol. Based on these data it is expected that the precursor compounds of the present invention will in the preparation of electronic devices allow for a much wider choice in solvents. In consequence it is expected that the preparation of electronic devices will be facilitated as the solvents that may be used may be less destructive on already formed layers of the electronic device.

Example 6

Transistor Fabrication and Performance Measurement

Bottom contact-top gate transistors having a channel width of 50 µm and a channel length of 1000 µm (see FIG. 3 for a schematic representation) were prepared on glass substrates, which had been cleaned with acetone and isopropanol in an ultrasonic bath. Au electrodes were deposited onto the glass substrates by thermal evaporation using a shadow mask. The resulting structures were then immersed for 1000 s in a 0.1 mmol/l solution of Jul-S-S-Jul 6 in chlorobenzene. Subsequently, in a glovebox under nitrogen atmosphere a n-type semiconductor (ActivInk™ N2200 [P(NDI2OD-T2)]), Polyera Corporation, Skokie, Ill., USA) was spin-coated thereon from a 10 mg/ml chlorobenzene solution and heated on a hot plate at 100° C. for 180 s. Then a dielectric layer of Parylene N was formed by vapor phase deposition using a PDS2010 Coating System by SPS™. Finally a ca. 100 nm thick Ag gate electrode was deposited by thermal evaporation onto the dielectric layer using a shadow mask. The resulting devices could be used as such under ambient conditions without any further encapsulation layer.

Thicknesses of the respective layers were determined with a Dektak profilometer with the following results:

TABLE 4

| | Thickness [nm] |
|---|---|
| Au source and drain electrodes | ca. 60 |
| Semiconductor layer (ActivInk™ N2200) | 80 ± 5 |
| Dielectric layer (Parylene-N) | 270 ± 10 |

Figure 5:
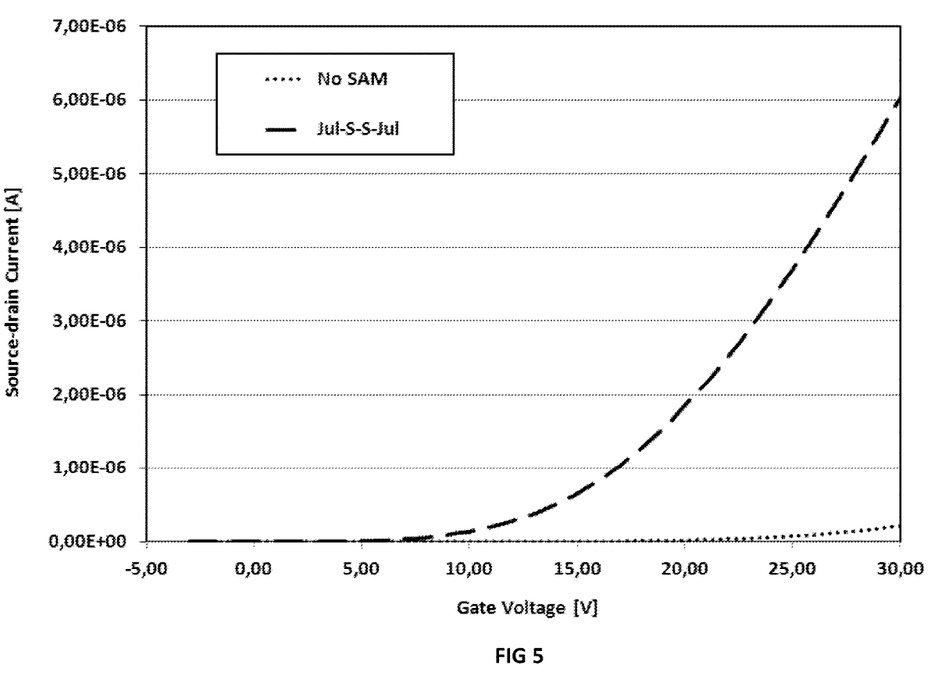
FIG. 5 shows the transfer characteristics of the transistor of Example 6.

Transistor transfer and output measurements were conducted in ambient atmosphere using an Agilent parameter analyzer with a source-drain voltage of 15 V. Transfer characteristics are shown in FIG. 5. Table 5 gives the respective contact resistances, channel resistances and threshold voltages.

TABLE 5

| Self-assembled monolayer Precursor Compound | Contact resistance [Ω cm] | Channel resistance [Ω cm$^{-1}$] | $V_{Threshold}$ [V] |
|---|---|---|---|
| No SAM (comparative) | 5.2 · 10$^6$ | 7.5 · 10$^9$ | 18.4 |
| Jul-S-S-Jul | 8.1 · 10$^4$ | 9.4 · 10$^8$ | 7.9 |

The results clearly show the advantages of the present invention. In comparison to the devices comprising the untreated Au source and drain electrodes the devices comprising the present self-assembled monolayer surprisingly show very much improved properties, namely increased currents at a given voltage (see FIG. 5). The positive effect of the presence of a self-assembled monolayer in accordance with the present application can also clearly be seen in the improvement in resistances, be it contact resistance as well as channel resistance. It is also noted that the threshold voltages are strongly shifted in the direction of 0.

The invention claimed is:

1. An organic electronic device comprising a self-assembled monolayer on a metal or metal oxide substrate, said self-assembled monolayer comprising a moiety of general formula (IB)

(IB)

wherein
$R^1$ is H, F, methyl, ethyl, methyl wherein one or more hydrogen is replaced by fluorine, ethyl wherein one or more hydrogen is replaced by fluorine, or —(C≡C)$_a$—(Ar$^1$)$_b$—(C≡C)$_c$—(R$^8$)$_d$—X$^5$—* with
Ar$^1$ being para-phenylene or a para-phenylene wherein one or more carbon ring atom is replaced by N;
$R^8$ being —CH$_2$— or —CF$_2$—;
$X^5$ being —X$^a$—, —X$^a$—X$^b$—, —C(=X$^a$)—X$^b$—, —X$^a$O$_3$—, —X$^a$—X$^b$O$_3$—, —PO$_2$H— or —PO$_3$H—, with X$^a$ and X$^b$ being independently of each S or Se;
a being 0, 1 or 2;
b being 0, 1 or 2;
c being 0, 1 or 2; and
d being 0, 1 or 2,
and
$R^2$ and $R^4$, are H.

2. An organic electronic device comprising a self-assembled monolayer according to-claim 1, wherein $X^5$ is —S—, —S—S—, —C(=S)—S—, —SO$_3$—, —S—SO$_3$—, —PO$_2$H— or —PO$_3$H—.

3. An organic electronic device comprising a self-assembled monolayer according to claim 1, wherein $X^5$ is —S—.

4. An organic electronic device comprising a self-assembled monolayer according to claim 1, wherein $R^8$ is —CH$_2$—.

5. An organic electronic device comprising a self-assembled monolayer according to claim 1, wherein Ar$^1$ is of formulae (II-1) to (II-7)

(II-1)

(II-2)

(II-3)

(II-4)

(II-5)

(II-6)

(II-7)

6. An organic electronic device comprising a self-assembled monolayer according to claim 1, wherein a is 0 or 1, b is 0 or 1, c is 0 or 1, and d is 0 or 1.

7. An organic electronic device comprising a self-assembled monolayer according to claim 1, wherein a+b+c+d≥1.

8. An organic electronic device according to claim 1, wherein the organic electronic device is an organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (OSC), photodiodes, laser diodes, photoconductors, organic photodetectors (OPD), electrophotographic devices, electrophotographic recording devices, organic memory devices, sensor devices, biosensors, biochips, security markings, security devices, or components or devices for detecting and discriminating DNA sequences.

9. A process for the preparation of the organic electronic device comprising a self-assembled monolayer of claim 1, said process comprising the steps of
(a) providing a metal surface or a metal oxide surface, and
(c) applying one or more precursor compound to said metal surface or metal oxide surface,
thus obtaining a self-assembled monolayer on said metal surface or metal oxide surface, wherein the precursor compound comprises a moiety of formula (IB)

(IB)

wherein
$R^1$ is H, F, methyl, ethyl, methyl wherein one or more hydrogen is replaced by fluorine, ethyl wherein one or more hydrogen is replaced by fluorine, or —(C≡C)$_a$—(Ar$^1$)$_b$—(C≡C)$_c$—(R$^8$)$_d$—X$^5$—* with
Ar$^1$ being para-phenylene or a para-phenylene wherein one or more carbon ring atom is substituted by N;
$R^8$ being —CH$_2$— or —CF$_2$—;
$X^b$ being —X$^a$—, —X$^a$—X$^b$—, —C(=X$^a$)—X$^b$—, —X$^a$O$_3$—, —X$^a$—X$^b$O$_3$—, —PO$_2$H— or —PO$_3$H—, with X$^a$ and X$^b$ being independently of each S or Se;
a being 0, 1 or 2;
b being 0, 1 or 2;
c being 0, 1 or 2; and
d being 0, 1 or 2,
$R^2$ and $R^4$ are H.

10. A process according to claim 9, wherein $R^1$ is H, F, methyl, ethyl, methyl wherein one or more hydrogen is replaced by fluorine, ethyl wherein one or more hydrogen is replaced by fluorine, or —(C≡C)$_a$—(Ar$^1$)$_b$—(C≡C)$_c$—(R$^8$)$_d$—X$^5$—H with
Ar$^1$ being para-phenylene or a para-phenylene wherein one or more carbon ring atom is substituted by N;
$R^8$ being —CH$_2$— or —CF$_2$—;
$X^5$ being —X$^a$—, X$^a$—X$^b$—, c(=X$^a$)—X$^b$—, —X$^a$—X$^b$O$_3$—,—PO$_2$ H— and —PO$_3$H—, with X$^a$ or X$^b$ being independently of each S or Se;
a being 0, 1 or 2;
b being 0, 1 or 2;
c being 0, 1 or 2; and
d being 0, 1 or 2.

11. A process according to claim 9, wherein two moieties of formula (IB) are linked by —(C≡C)$_a$—(Ar$^1$)$_b$—(C≡C)$_c$—(R$^8$)$_d$—S—S—(R$^8$)$_d$—(C≡C)$_c$—(Ar$^1$)$_b$—(C≡C)$_a$—.

12. A process according to claim 9, wherein the precursor compound comprises a moiety of formula (IB) wherein
$X^5$ is —S—, —S—S—, —C(=S)—S—, —SO$_3$—, —S—SO$_3$—, —PO$_2$H— or —PO$_3$H—.

* * * * *